United States Patent [19]

Den Otter et al.

[11] 4,140,660
[45] Feb. 20, 1979

[54] PROCESS OF PREPARING A FLAME-RETARDANT POLYURETHANE AND PRODUCT PRODUCED THEREFROM

[75] Inventors: Marinus J. A. M. Den Otter, Munstergeleen; Albert A. Van Geenen; Anne Te Mijenhuis, both of Brunssum, all of Netherlands

[73] Assignee: Stamicarbon, B.V., Geleen, Netherlands

[21] Appl. No.: 843,062

[22] Filed: Oct. 17, 1977

Related U.S. Application Data

[62] Division of Ser. No. 678,438, Apr. 19, 1976, Pat. No. 4,085,283.

[30] Foreign Application Priority Data

Apr. 19, 1975 [NL] Netherlands ................7504684

[51] Int. Cl.² ........................................... C08G 18/14
[52] U.S. Cl. ................................. 162/159; 521/902; 521/165; 528/72; 162/164 R; 252/8.1; 260/45.8 NT; 260/DIG. 24; 544/214

[58] Field of Search .................. 260/2.5 AW, 2.5 AJ, 260/2.5 AR, 2.5 AQ, 77.555

[56] References Cited

U.S. PATENT DOCUMENTS 3,121,082    2/1964    Guttag ........................... 260/2.5 AW Primary Examiner—Morton Foelak
Attorney, Agent, or Firm—Cushman, Darby & Cushman

[57] ABSTRACT

Flame-retarding compounds are disclosed which are of the formula

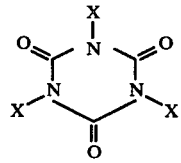

wherein X is a phosphorus derivative.

7 Claims, No Drawings

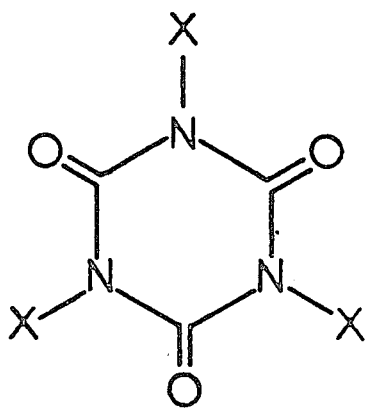

PROCESS OF PREPARING A FLAME-RETARDANT POLYURETHANE AND PRODUCT PRODUCED THEREFROM

This is a division of application Ser. No. 678,438 filed Apr. 19, 1976.

The invention relates to new compounds having flame-retarding properties and to the process of preparing those compounds. The invention further relates to a process for preparing flame-retarding compositions, e.g., polymer compositions, textile, paper, etc., by simply adding and/or by incorporating by polymerization the new compounds into polymers, polymer compositions, textile, paper, etc., as well as to flame-retarding compositions prepared this way.

Many methods for rendering polymers or polymer compositions, textile, paper, etc., flame-retarding are known. However, each of these methods has an inherent disadvantage. There is a need for a simple method for preparing flame-retarding textile and flame-retarding polymer compositions.

An art recognized method for imparting the flame-retarding property to textiles, papers and polymers is by way of incorporating an additive or a dressing agent, consisting of a chlorinated hydrocarbon in combination with antimony oxide or an organic antimony compound. This method involves the disadvantage that properties, other than the flame-retarding characteristics, of the textile or the polymer composition, modified in this manner, are adversely affected.

SUMMARY OF THE INVENTION

The invention relates to a new compound having flame-retarding properties of the formula:

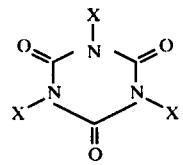

in which at least one of the groups X is $-Y-P(O)(OR)_2$ and the two other groups X, independent of each other, are a hydrogen atom, a halogen atom, an alkyl group with at most 6 carbon atoms or $-Y-P(O)(OR)_2$ or $-Y-OH$, the symbol Y representing an alkylene group or alkyl- or halogen-substituted alkylene group of at most 6 carbon atoms or a poly-oxyalkylene group consisting of 2-4 oxy-alkylene units with 1-3 carbon atoms per unit, and in which each group R, independent of each other is a phenyl group or an alkyl or cyclo-alkyl group with at most 6 carbon atoms or such phenyl, alkyl or cyclo-alkyl group which contains one or more halogen substituente. Preferably, R is methyl, ethyl or (iso)-propyl, more preferably chloromethyl, 2-chloroethyl or 2,3-dibromopropyl.

DESCRIPTION OF THE INVENTION

The invention is directed to compounds of the formula

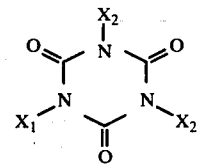

in which each of $X_1$, $X_2$, and $X_3$ is hydrogen, halogen, alkyl of 1 to 6 carbon atoms, $-Y-P(O)(OR)(OR')$ or $-Y-OH$, wherein Y is alkylene or alkyl- or halogen-substituted alkylene of 1 to 6 carbon atoms; or polyoxyalkylene wherein each oxyalkylene unit contains 1 to 3 carbon atoms and wherein said polyoxyalkylene contains 2 to 4 of said units; wherein each of R and R' is phenyl, or (cyclo)-alkyl of 1 to 6 carbon atoms, or such phenyl, alkyl or cycloalkyl containing one or more halogen substituents; and in which at least one of said $X_1$, $X_2$ or $X_3$ is $-Y-P(O)(OR)(OR')$. The halogen is preferably chlorine or bromine. Preferably, each of R and R' is methyl, ethyl or (iso)propyl, more preferably chloromethyl, 2-chloroethyl or 2,3-dibromopropyl.

Compounds of this kind can be prepared by reacting an isocyanuric acid derivative of formula (1), in which at least one of $X_1$, $X_2$, or $X_3$ represents $-YOH$, is reacted with a phosphite of the formula $P(OR)_3$, R being as defined above. Such a reaction can be carried out at an elevated temperature, for instance between 30° and 200° C., as a rule, preferably between 80° and 120° C. A diluent or solvent may be used, but is not essential. Examples of suitable solvents are lower alcohols, glymes and other polyfunctional ethers, dimethylformamide or mixtures of said diluents with aliphatic or aromatic hydrocarbons. The reaction pressure is not critical, so that preferably the reaction is undertaken at atmospheric pressure.

Higher and lower pressures, for instance between 0.1 and 10 atmospheres, can be employed. Usually, the reaction takes 1 – 12 hours. After the reaction is complete, the product may be recovered by removal of the volatile components from the reaction mixture, for instance, by evaporation.

Preferably, -hydroxyethyl) reactants for the preparation of compounds according to the invention are hydroxyalkylated isocyanuric acid derivatives. Such reactants include, for instance, tris (hydroxymethyl) isocyanurate (THMIC), tris (2-hydroxy-ethyl) isocyanurate (THEIC), tris (2-hydroxy-propyl) isocyanurate (THPIC), bis (hydroxymethyl) isocyanurate, mixtures of hydroxymethylated and/or -hydroxypropyl) and/or hydroxypropylated isocyanuric acids and the like. Reactants in addition to THMIC, THEIC and THPIC which may be used are those products which are not quite stoichiometric adducts of (1) cyanuric acid and, (2) formaldehyde, ethylene oxide or propylene oxide, such as obtained in known processes for preparing THMIC, THEIC and THPIC. Those products of (1) and (2) which are not stoichiometric adducts are mixtures of tris (hydroxyalkyl) isocyanurate and bis (hydroxyalkyl) isocyanurate and/or, generally, minor amounts of these compounds in which one or more hydroxyalkyl groups have been replaced by polyoxyalkylene groups consisting of 2-4 oxyalkylene units and/or by oligomers obtained by condensation of the above-mentioned compounds.

THEIC is an isocyanuric acid derivative which is commercially available and suitable as starting material for preparation of compounds having flame-retarding properties according to the invention. THEIC may be prepared in a known way by reaction of cyanuric acid and ethylene oxide. A disadvantage of THEIC is the difficulty of handling THEIC as a result of its high melting point. Analogously, like THEIC, THPIC can be prepared by reaction of cyanuric acid with propylene oxide.

THMIC is a particularly preferred reactant for forming the compound of the invention. This substance can be prepared in a very simple way, starting from inexpensive feedstocks, and can be handled easily.

THMIC can be prepared by reacting cyanuric acid with formaldehyde or with a compound which splits off formaldehyde, such as paraformaldehyde. The reaction may be effected in water or in a, mainly inert, polar solvent or mixture of solvents. Suitable solvents are, e.g., nitriles and ketones, like acetonitrile, cyclohexanone, methylethylketone, or, for instance, dimethylformamide, dioxane or pyridine. Since dimethylformamide is at the same time an extremely suitable diluent for the reaction of THMIC with an organic phosphite to form the required compound having flame-retarding properties, this solvent is preferably used. The reaction of cyanuric acid and paraformaldehyde in an organic solvent generally proceeds more rapidly if a small catalytic quantity of acid or base is present. The reaction can be carried out at a temperature of up to 100° C., preferably at 50° to 90° C. The pressure of the reaction is not critical, both atmospheric pressure and higher pressures being suitable. The ratio between the reactants may vary between a molar formaldehyde to cyanuric acid ratio of 1.5 : 1 and 10 : 1. Preferably, a ratio between 2 : 1 and 5 : 1 is chosen. The pH value seems to have little influence on the course of the reaction; and, when water is the solvent, the pH may vary between 1 and 7; however higher pH values, e.g., up to 10, may be used if desired.

After termination of the THMIC-forming reaction, the solvent can be removed either wholly or partly, for instance by evaporation at a reduced pressure. In the latter case, a temperature below 60° C. is employed, preferably around 50° C. If the preparation has taken place in water, the water may be replaced by an inert organic solvent which is suitable for the subsequent reaction with an organic phosphate, for instance, by means of azeotropic distillation. Preferably, the reaction between THMIC and the organic phophite is undertaken in the same solvent as has been used in the preparation of the THMIC.

Since THMIC starts to decompose at a temperature above about 90° C., the reaction with the organic phosphite is preferably undertaken at a lower temperature, for instance between 60° and 90° C.

Reactions between other hydroxyalkylated isocyanuric acids and organic phosphites can be carried out in an analogous manner.

Compounds having flame-retarding properties according to the invention are also considered to include the reaction products of (1) a phosphite of the formula $P(OR)_3$ and (2) by-products produced in the reaction of (a) hydroxylated isocyanuric acid and (b) formaldehyde, ethylene oxide or propylene oxide, on reaction in non-stoichiometric quantities. These products, which are not quite stoichiometric, consist of mixtures of different compounds of formula I above, in which X ($X_1$, $X_2$, $X_3$), Y and R have the meanings indicated above.

If the compound having flame-retarding properties to be prepared is to contain an average number of phosphonate groups per cyanuric acid moiety which is as large as possible, i.e., as close as possible to 3, it is advantageous to use an excess amount of phosphate relative to the stoichiometric quantity, for instance an excess of 50 – 100% relative to the quantity calculated for 3 phosphonate groups per cyanuric acid moiety. Moreover, it is advantageous in that case, particularly if a hydroxymethylated isocyanuric acid like THMIC is employed as a starting material, which THMIC may relatively easily lose one or more methylol groups, that a hydroxyalkylated isocyanuric acid be started from which, statistically, contains more than three oxyalkylene groups per cyanuric acid moiety, for instance 3.1 – 5 oxyalkylene groups, particularly oxymethylene groups, per cyanuric acid moiety. Finally, it is also important that the reaction between phosphite and hydroxyalkylated isocyanuric acid be undertaken at a temperature which is as low as possible in order to avoid intermediate split-off of oxyalkylene groups.

In this way it is possible to prepare compounds which approximately satisfy formulae like formula (2) and formula (3) below:

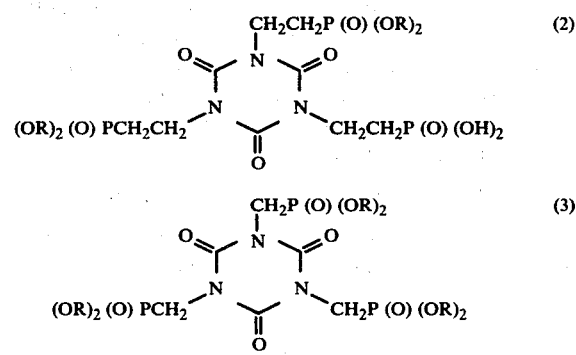

Compounds like that according to formula (5) below:

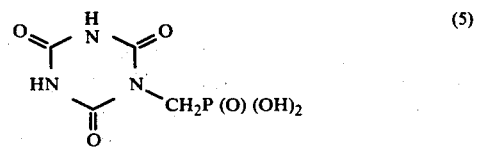

can be prepared by reaction of 1 mole of phosphite and 1 mole of the relevant hydroxyalkylated isocyanuric acid, followed by thermal split-off of the non-converted (poly)oxyalkylene groups. To this end, in the case of hydroxymethylated isocyanuric acid derivatives like those derived from THMIC, heating at 100° C., or higher, for instance 100° – 150° C., preferably in vacuo, will suffice. If one proceeds in an analogous way, but now causes 2 moles of phosphite, instead of 1, to react with 1 mole of hydroxyalkylated isocyanuric acid prior to having the uncoverted (poly)oxyalkylene groups split-off, one obtains compounds of the type of formula (4), which formula stands for the derivative produced from hydroxymethylated isocyanuric acid:

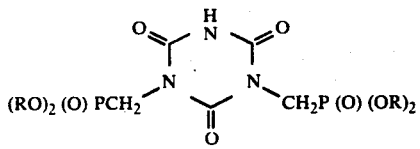

(4)

It is advisable that a certain excess amount of phosphite, for instance an excess of 25 - 50%, be then used.

Compounds of the type of formula (6) and formula (7)

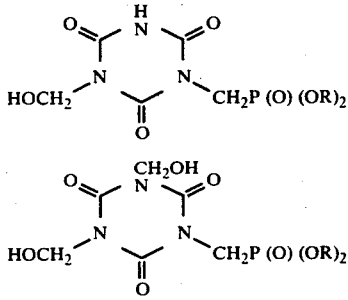

are obtained in a way analogous to the above disclosure describing the process for producing compounds of formula (5), however, without, or with only a partial, split-off of non-converted (poly)oxyalkylene groups.

Thermal split-off of (poly)oxyalkylene groups other than (poly)oxymethylene groups is difficult. Compounds of the type of the formulae 4 -7 wherein in lieu of the methylene groups higher alkylene groups or alkylene-(poly)oxyalkylene groups with 2 or more carbon atoms per alkylene group are present can preferably be prepared by reaction of a phosphite of the formula $P(OR)_3$ with a hydroxyalkylated isocyanuric acid which is hydroxy-alkylated with less than 3 moles of the appropriate alkylene oxide per cyanuric acid moiety. Particularly the diphosphonate products can well be prepared by this method.

The compounds provided by the invention have flame-retarding properties and can be used for preparing flame-retarding textile and paper and flame-retarding polymer compositions.

For preparing flame-retarding textile or paper, one or more of the compounds provided by the invention are applied, in a quantity capable of sufficient flame-retardation, to a normal flammable textile material or paper. The textile material may both be of natural origin, loke a cellulose material, and have been wholly or partly prepared synthetically, such as polyacrylonitrile, nylon-6, nylon-6,6, rayon, and the like.

For preparing flame-retarding polymer compositions according to the invention, one or more of the compounds provided by the invention are, according to one embodiment, added in a flame-retarding quantity to a polymer or a polymer composition.

Any of the various polymers or polymer compositions may be treated, for instance a polyolefin, like polyethylene, polypropylene, polybutylene-1, and poly-4-methylpentene-1; a copolymer of one or more olefins, like a crystalline copolymer of ethylene and propylene, a rubber-like copolymer of ethylene, propylene and cyclopentadiene as the third monomer; a homo- and co-polymer of alkenylaromatic compounds, such as polystyrene and polymethylstyrene; a copolymer of an alkenyl-aromatic compound and butadiene and/or acrylonitrile, such as a rubber-like styrene-butadiene copolymer, a copolymer of styrene and acrylonitrile or a graft copolymer of styrene and/or acrylonitrile on polybutadiene (ABS resin); acrylic polymers, like polyethyl acrylate and polymethylmethacrylate; a cellulose derivative, such as cellulose acetate and cellulose nitrate; a phenolformaldehyde resin; a urea-formaldehyde resin; a melamine-formaldehyde resin; a polyamide; a polyester; polyvinylchloride; polyformaldehyde; butyl rubber, polyisoprene and other kinds of rubber; an epoxy resin; a polycarbonate, etc.

Preferably, however, the polymer is a polyurethane, more particularly a polyisocyanurate foam, since the compounds provided by the invention can well be combined therewith. Examples of polymers to be considered in particular are the reaction products of, on the one hand, toluylene diisocyanate or methylene bis(phenylene isocyanate) or higher homologues thereof and, on the other, a polyetherpolyol, obtained for instance on the basis of starch derivatives, tall oil, etc., or a polyester polyol.

Generally, the present compounds can be incorporated in the polymer in a quantity of 5 - 50% by weight, preferably 20 - 40% by weight based on the polymer.

The method of addition may be an arbitrary, known method for incorporation of an additive in a polymer, for instance coating, mixing in powder form, and the like.

According to another embodiment a flame-retarding polymer composition is prepared in that a polymer is prepared having for (co)monomer a flame-retarding quantity of a compound of formula 1, in which X, Y and R have the meanings already indicated, and in which at least one of the X groups is a YOH group.

A monomer of this kind has an alcohol function and can be incorporated via this function into various polymers by polymerization, like in a polyester, a polyamide or a formaldehyde resin. Preferably, such a monomor is incorporated in a polyurethane, more particularly in a polyisocyanurate, by polymerization. Examples of suitable polyurethanes and polyisocyanurates have been indicated above.

Firm anchoring of the monomer having flame-retarding properties is achieved particularly if a monomer is used in which two of the groups X have the composition —YOH. Of course, a monomer of this kind is bi-functional in the polymerization reaction.

In addition to flame-retarding compound of the invention, the polymer composition may contain other usual additives, like fillers, dyes, pigments, stabilizing agents, antistatic agents and plasticizers.

The invention will be illustrated in the following examples, but is not limited to the embodiments described therein but is to be construed as encompassing all equivalents and alternatives known to the art.

PREPARATION A-D

Preparation of tris(hydroxymethyl)isocyanurate

A. A suspension of 516 g of cyanuric acid in 1200 g of 30% formalin was heated to 80° C., whilst stirred. Next, the reaction mixture was maintained at this temperature for 30 more minutes, during which time all cyanuric acid dissolved. The reaction mixture was then cooled to 60° C., whereupon, at 55° C., and reduced pressure (about 15 mm Hg), the reaction mixture was concentrated by evaporation to a viscous, clear liquid.

Analysis produced the following results:

| | |
|---|---|
| Isocyanurate groups (determined as cyanuric acid) | 58.1% by weight |
| Methylol groups (determined as $CH_2O$) | 37.1% by weight |
| Water | 4.0% by weight |
| Molar $CH_2O$ to cyanuric acid ratio | 2.75 : 1 |

During the analysis the methylol groups were converted — by pyrolysis in phosphoric acid — into formaldehyde and determined as such. The water content was determined by Fischer titration. Cyanuric acid was determined by diluting the tris(hydroxymethyl) isocyanurate with an excess amount of water and by causing the cyanuric acid to precipitate through addition of melamine.

B. In the way described under A., 850 g of tris(hydroxymethyl) isocyanurate having a water content of 7.0% by weight was prepared, to which 250 ml of acetone was added. At 55° C., with slow reduction of the pressure to an ultimate value of 15 mm Hg, the mixture was subjected to azeotropic distillation. This procedure was repeated six more times. Eventually, a clear, viscous liquid was obtained. Analysis produced the following results:

| | |
|---|---|
| Cyanuric acid | 53.6% by weight |
| Formaldehyde | 35.0% by weight |
| Water | 1.4% by weight |
| Acetone | 9.0% by weight |
| Molar $CH_2O$ to cyanuric acid ratio | 2.8 : 1 |

C. A suspension of 23.6 g of paraformaldehyde (96%) and 32.5 g of cyanuric acid in 55 ml of water-free dioxane was heated to 80° C., 1 ml of acetic acid was added and the reaction mixture was heated for 45 more minutes at 80° C., whereupon the mixture was cooled to 60° C. By means of concentration by evaporation at 55° C. and a reduced pressure a clear, viscous liquid was obtained. Analysis produced the following results:

| | |
|---|---|
| Cyanuric acid | 46.7% by weight |
| Formaldehyde | 30.6% by weight |
| Acetic acid | 0.6% by weight |
| Dioxane | Not determined |
| Molar $CH_2O$ to cyanuric acid ratio | 2.8 : 1 |

D. A suspension of 516 g of cyanuric acid and 375 g of paraformaldehyde (96%) in 800 ml of dry N,N-dimethylformamide was heated to 80° C., whereupon 3 ml of triethylamine was added. After the reaction time of 90 minutes at 80° C., the reaction mixture was cooled and concentrated by evaporation at a reduced pressure (approximately 1 mm Hg). A clear, viscous liquid was obtained. Analysis produced the following results:

| | |
|---|---|
| Cyanuric acid | 44.9% by weight |
| Formaldehyde | 28.2% by weight |
| Water | 0.06% by weight |
| Dimethylformamide | 25.0% by weight |
| Molar $CH_2O$ to cyanuric acid ratio | 2.7 : 1 |

EXAMPLE I

Preparation of monophosphonate product from THMIC and trimethyl phosphite

At 70° C., in 2½ hours, 360 ml of trimethyl phosphite were added dropwise, with stirring, to 1154 g of THMIC reaction product, which had been obtained in accordance with Preparation D. After complete addition, stirring was continued for 4 more hours at 70° C. After cooling, the volatile components were evaporated off at 1 mm Hg in a rotating evaporator. The maximum temperature during this procedure amounted to 60° C.

Proton nuclear spin resonance proved that the viscous liquid obtained contained practically all phosphor bound as monophosphonate groups and consisted of a mixture of the compounds of the formulae (6) and (7) of the sheet of formulae (R = $CH_3$), and in addition a small quantity of the corresponding monophosphite product and some dimethylformamide. The content of methylol groups amounted to 14.5% by weight, determined as formaldehyde.

EXAMPLE II

Preparation of diphosphonate product from THMIC and trimethyl phosphite

At 70° C., in 2½ hours, 700 ml (5.9 moles) of trimethyl phosphite was added dropwise, with stirring, to 577 g of THMIC (2 moles), prepared in accordance with Preparation D. After complete addition, stirring was continued for 4 more hours at 70° C., whereupon the volatile components were evaporated off at 1 mm Hg and a maximum temperature of 100° C., in a rotating evaporator.

A slightly viscous liquid was obtained. Proton nuclear spin resonance proved that the product consisted of the diphosphonate product of formula (4) of the sheet of formulae (R = $CH_3$), contaminated by a small amount of phosphite product. The solvent content amounted to approximately 1% by weight; the phosphor content of the product appeared to be 14.8% by weight. (The calculated phosphor content for formula (4) with R = $CH_3$ amounts to 15.5% by weight).

EXAMPLE III

Preparation of triphosphonate product from THMIC and tris(2-chloroethyl) phosphite At 65° C., in 1½ hours, 122 g of tris(2-chloroethyl) phosphite were added dropwise, with stirring, to 41.5 g of THMIC prepared in aacordance with Preparation D. After complete addition, stirring was continued for 3 hours at 70° C. After this time the conversion on the basis of phosphite was 75%. The volatile components were evaporated off at 1 mm Hg and a maximum temperature of 100° C. in a rotating evaporator.

A slightly viscous liquid was obtained, which consisted largely of the triphosphonate product of formula (3) (R = 2-chloroethyl) and a smaller quantity of the diphosphonate product of formula (4) (R = 2-chloroethyl). The liquid contained 25% unconverted tris (2-chloroethyl) phosphite, 10% THMIC and some dimethylformamide.

EXAMPLE IV

Preparation of monophosphonate product from THMIC and tris (2-chloroethyl phosphite At 70° C., in 1 hour, 67 g of tris (2-chloroethyl) phosphite were added dropwise, with stirring, to 64 g of THMIC prepared in accordance with Preparation D. After complete addition, stirring was continued for 4.5 hours. After cooling the volatile components were evaporated off at 1 mm Hg and a maximum temperature of 60° C. in a rotating evaporator.

A viscous liquid was obtained, which consisted of a mixture of the monophosphonate products of formulae (6) and (7) (R = 2-chloroethyl), and in addition a small quantity of THMIC and 8% by weight of dimethylformamide.

EXAMPLE V

Preparation of a flame-retarding polyisocyanurate foam by incorporation by polymerization of flame-retarding monophosphonate according to the invention A polyisocyanurate foam was prepared by mixing — in a beaker, with the aid of a fast stirrer — 100 g of the monophosphonate product obtained in Example I with 1 g of the emulsifier L 4350 (marketed by Union Carbide Corp.), 2 ml of triethylamine, 5 g of methylene chloride, and 73 g of polymethylenepolyphenylisocyanate, which is marketed under the name of Desmodur 44 V. The hard, fine-cellular foam obtained this way showed an oxygen index of 25, which was determined according to ASTM-D 2863-70.

EXAMPLE VI

Preparation of a flame-retarding polyiscyanurate foam with diphosphonate according to the invention A polyisocyanurate foam was prepared in the way described in EXAMPLE V, starting from 100 g of THMIC obtained in accordance to Preparation D, 20 g of diphosphonate product (prepared in accordance with Example II), 1 g of emulsifier L 5340, 0.2 ml of dibutyltindiacetate, 5 g of methylene chloride, and 152.7 g of polymethylenepolyphenylisocyanate. The hard, slightly resilient, fine-cellular foam obtained this way showed an oxygen index of 23.5, determined according to ASTM-D 2363-70.

EXAMPLE VII

Preparation of a flame-retarding polyisocyanurate foam with chlorine-containing triphosphonate according to the invention A polyisocyanurate foam was prepared in the way described in Example V, starting from 100 g of THMIC obtained in accordance with Preparation D, 20 g of triphosphonate product prepared in accordance with Example III, 1 g of emulsifier L 5340, 0.2 ml of dibutyltindiacetate, 20 g of methylene chloride, and 162 g of polymethylene-polyphenylisocyanate. The hard, slightly resilient fine-cellular foam obtained in this way had a density of 40 kg/$^3$m and an oxygen index of 23.5, determined according to ASTM-D 2863-70.

Although the amount of flame-retarding compound present in the polyisocyanurate foam in this case was only 3.8% by weight compared to 7.2% by weight in Example VI, the oxygen index was equal in both cases.

COMPARATIVE EXPERIMENT

In the way described in Example V, a polyisocyanurate foam was prepared, starting from 100 g of THMIC obtained in accordance with Preparation D, 1 g of emulsifier L 5340, 0.2 ml of dibutyltindiacetate, 5 g of methylene chloride, and 162 g of polymethylenepolyphenylisocyanate. The hard, fine-cellular foam obtained this way had a density of 40 kg/m$^3$ and an oxygen index of 21.5, determined according to ASTM-D 2863-70.

What is claimed is:

1. A process for preparing a flame-retarding urethane polymer, which consists essentially in co-polymerizing a flame-retarding quantity of a compound of the formula

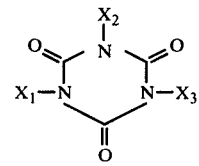

in which each of $X_1$, $X_2$ and $X_3$ is hydrogen, halogen, alkyl of up to 6 carbon atoms, —Y—P(O)(OR)(OR') or —Y—OH, wherein Y is (1) alkylene, (2) alkyl-substituted alkylene, (3) halogen-substituted alkylene wherein each of said alkyl and said alkylene contains from 1 to 6 carbon atoms; or (4) polyoxyalkylene in which each oxyalkylene unit contains 1 to 3 carbon atoms and wherein said polyoxyalkylene contains 2 to 4 of said oxyalkylene units; wherein each of R and R' is phenyl, alkyl or cycloalkyl wherein said alkyl and said cycloalkyl contain 1 to 6 carbon atoms, wherein each of said phenyl, alkyl or cycloalkyl is unsubstituted or substituted by at least one halogen atom, and wherein the Y group is bonded to both the ring nitrogen atom and the phosphonate phosphorus atom via a carbon atom; and in which at least one of said $X_1$, $X_2$ or $X_3$ is —Y—P-(O)(OR)(OR') and at least one of said $X_1$, $X_2$ or $X_3$ is —Y—OH, with a copolymerizable organic monomer having a functional isocyanate group reactive therewith.

2. The process of claim 1, wherein at least two of $x_1$, $X_2$ or $X_3$ are —Y—OH.

3. The process of claim 1, wherein said compound has the formula

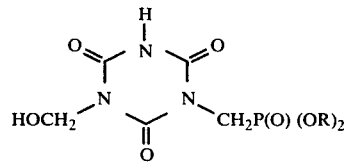

4. The process of claim 1, wherein said compound has the formula

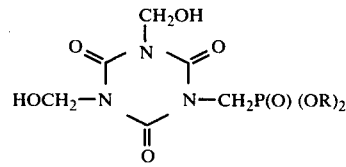

5. The process of claim 1, wherein said polyurethane is a polyisocyanurate foam.

6. A flame-retarding polymer according to the process of claim 1.

7. A textile or paper composition containing a flame-retarding quantity of the polymer of claim 6.

* * * * *